Figure 1:
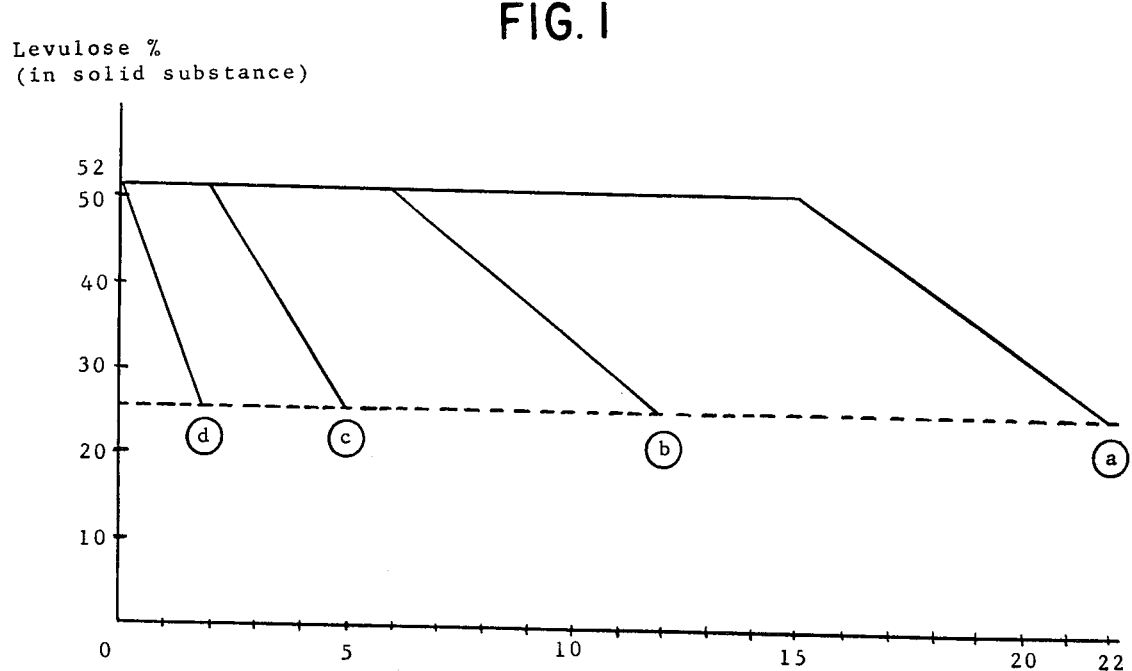

United States Patent [19]

Tamura et al.

[11] 3,960,663
[45] June 1, 1976

[54] PROCESS FOR THE CONTINUOUS ISOMERIZATION OF DEXTROSE

[75] Inventors: Masaki Tamura, Machida; Soichiro Ushiro, Kokubunji; Shiro Hasagawa, Tama, all of Japan

[73] Assignee: CPC International Inc., Englewood Cliffs, N.J.

[22] Filed: Sept. 13, 1974

(Under Rule 47)

[21] Appl. No.: 505,823

[30] Foreign Application Priority Data

Sept. 13, 1973 Japan.............................. 48-102748

[52] U.S. Cl. ............................... 195/31 F; 195/63; 195/68; 195/115; 195/116
[51] Int. Cl.² ........................................ C12D 13/00
[58] Field of Search ....... 195/31 F, 63, 68, DIG. 11, 195/116, 115

[56] References Cited
UNITED STATES PATENTS

| | | |
|---|---|---|
| 3,708,397 | 1/1973 | Sipos ..................................... 195/68 |
| 3,788,945 | 1/1974 | Thompson et al................. 195/31 F |
| 3,791,927 | 2/1974 | Forgione et al....................... 195/63 |
| 3,915,797 | 10/1975 | Ishimatsu et al.................. 195/68 X |

OTHER PUBLICATIONS

Tsumura et al., "Continuous Isomerization of Glucose by a Column of Glucose Isomerase", J. of Food Sci. and Tech., Vol. 14, No. 12, pp. 539-540 (1970).
Zaborsky, *Immobilized Enzymes,* CRC Press, 1973, pp. 75-82.

*Primary Examiner*—A. Louis Monacell
*Assistant Examiner*—Thomas G. Wiseman
*Attorney, Agent, or Firm*—Albert P. Halluin; Donald G. Marion

[57] ABSTRACT

The continuous isomerization of dextrose to levulose is efficiently conducted in a fixed bed reactor, whose bed is charged with immobilized dextrose isomerase, by periodically adding fresh isomerase to the feed liquor. The carrier, on which the isomerase is immobilized, binds the fresh isomerase, so that enzyme activity is maintained in the reactor at an effective level, without interrupting operations.

6 Claims, 2 Drawing Figures

PROCESS FOR THE CONTINUOUS ISOMERIZATION OF DEXTROSE

INTRODUCTION

This invention relates to a process for isomerizing dextrose to levulose with dextrose isomerase, especially to a method of isomerizing dextrose continuously with immobilized dextrose isomerase prepared by having the isomerase adsorbed on MR (macroreticular) type or porous type strongly basic anion exchange resins.

BACKGROUND

In recent years, various enzymes have been immobilized by various methods and continuous enzymatic reactions have been attempted with the resulting immobilized enzymes. It is possible to increase efficiency and to reduce labor costs, as well as to reduce equipment investment, by carrying out continuous enzymatic reactions with such immobilized enzymes. However, in the continuous isomerizaton reactions by means of columns packed with immobilized enzymes, it is very difficult to reactivate the enzymes when the activity drops, without suspending the reactions.

The present invention is particularly concerned with the continuous isomerization of dextrose to levulose, utilizing an immobilized form of dextrose isomerase, to produce levulose-bearing products.

DEFINITIONS

Because of the plethora of terms that are in common use in the art, a few definitions are made to clarify what has been said in the present application.

D. E.

The term "D.E." is an abbreviation of "dextrose equivalent," and these terms are used interchangeably to refer to the reducing sugar content of a material calculated as dextrose and expressed as percent of total solids.

STARCH HYDROLYZATE

The term "starch hydrolyzate" is used to refer to a syrup or dry product that is made by the hydrolysis of starch. Such a product may be made by acid or enzymatic hydrolysis. A preferred type of starch hydrolyzate for use for isomerizaton in accordance with the present invention is produced by acid or enzyme thinning to a D.E. of 10 or less, followed by enzymatic saccharification to a D.E. about 95 and preferably above 97.5.

GLUCOSE AND DEXTROSE

Medium D.E. starch hydrolyzates are commonly referred to in the art as "glucose," whether the starch hydrolyzate is in the form of a syrup or in the form of solids. The term "dextrose" is commonly reserved for the refined crystalline monosaccharide that is recovered from a high D.E. starch hydrolyzate, or for D-glucose as a constituent of starch hydrolyzates. As used herein, the term "dextrose" embraces this monosaccharide in any form, in solution or dry, as a constituent of a starch hydrolyzate syrup, syrup solids, or in refined crystalline form.

ERUCTOSE AND LEVULOSE

The terms "fructose" and "levulose" are generally employed interchangeably in the art to refer to the isomer of dextrose that is sweeter than dextrose. This isomer is found in honey and in invert sugar, along with dextrose, and it is valuable because of its sweetness. The term "levulose" has been used herein, to refer to this monosaccharide.

DEXTROSE ISOMERASE

The enzyme that isomerizes dextrose to levulose has been referred to in the art by several names. It is referred to in the Marshall U.S. Pat. No. 2,950,228, as xylose isomerase, because it isomerizes xylose to xylulose. This activity is in addition to its ability to isomerize dextrose to levulose. It has also been referred to in the art as dextrose isomerase and glucose isomerase. The terms "dextrose isomerase", or more briefly, "isomerase", have been used herein.

BRIEF SUMMARY OF THE INVENTION

The inventors conducted a series of studies on the immobilization of dextrose isomerase and also on the continuous isomerization of dextrose into levulose with the resulting immobilized dextrose isomerase.

As the result, they found that in the case of isomerization of dextrose into levulose by flowing continuously a dextrose-containing solution, the pH of which has been previously preferably adjusted to around 8.0, through the column packed with immobilized isomerase prepared by contacting a dextrose isomerase solution with either MR or porous type strongly basic anion exchange resins and adsorbing the enzyme thereon, when the activity of the immobilized enzyme drops and consequently the rate of isomerizaton also drops, it is possible to reactivate the enzyme by adding isomerase to the supply of dextrose-containing solution, without suspending the isomerization reaction, and the continuous isomerization can be carried out without interruption.

This invention is a method of continuous isomerization characterized by repetition of the enzyme resupply procedure, as necessary for continuous operation at a desired level of throughput and isomerization, in a given reactor under a desired set of isomerization conditions. In the course of continuous isomerizaton of dextrose into levulose by passing a dextrose solution, adjusted preferably to a pH value in the neighborhood of 8.0, through a column packed with immobilized dextrose isomerase prepared by having the isomerase adsorbed on MR type or porous-type anion exchange resins, fresh dextrose isomerase is added to the dextrose-containing solution to be passed through the column when the activity of the immobilized enzyme has dropped down to a certain degree. With the immobilized enzyme reactivated in this way, the dextrose-containing supply solution (without isomerase) is then passed through the column.

GENERAL DESCRIPTION OF THE INVENTION

THE ENZYME

The process of the present invention can be employed, so far as is know, for the production of immobilized enzyme preparations from all types of dextrose isomerase, including those where the enzyme has a dominant or more rapid catalytic action on an isomerizaton other than that of dextrose to levulose. The isomerase enzyme can be derived from a large number of different microbial sources.

Dextrose isomerase useful in this invention may originate, for example, in the cells of ray fungi (for example, *Streptomyces albus*) or bacteria (for example, *Lactobacillus brevis*)known as dextrose isomerase producing microorganisms. It is used in the different forms of crude isomerase extracted from the cells of the producing microorganisms by autolysis or by supersonic treatment and then separated from the debris of cells, or as partially purified isomerase obtained by removing nucleic acid present in crude isomerase with protamine, or as crystalline isomerase obtained by crystallization from partially purified isomerase which has been further purified by fractionation with ammonium sulfate.

Each enzyme seems to have its own particular characteristics, such as, for example, optimum pH, optimum temperature, the required metal ions, Michaelis constant, and the mechanism of levulose formation, all of which seem to be somewhat different from one enzyme to another. However, the process of the present invention seems to be useful with immobilized isomerase enzyme preparations from all known microbial sources, and more specifically, from all Streptomyces species and strains and all Bacillus species and strains that produce dextrose isomerase enzyme preparations.

Preferred microorganisms, for producing suitable isomerase for use in practising this invention, are the members of the Streptomyces genus. Particularly preferred species among this genus are *S. venezuelae* and *S. olivochromogenes*. Cultures of preferred strains of these organisms have been deposited in the American Type Culture Collection, Washington, D.C., and added to its permanent collection of microorganisms. They have been assigned the following indentification: *S. venezuelae* ATCC 21,113 and *S. olivochromogenes* ATCC 21,114.

The most preferred microorganisms are mutant strains of *Streptomyces olivochromogenes*, especially, *S. olivochromogenes* ATCC Nos. 21,713, 21,714, 21,715 and their equivalents. These microorganisms form appreciable quantities of isomerase when cultivated in nutrient media free of xylose and xylose-supplying material and free of added cobalt.

One unit of enzyme activity is defined as the amount of the enzyme activity which forms one micromole of levulose in one minute under the isomerization conditions described hereafter. To prepare an enzyme for assay, it is first necessary to convert it to a soluble form. A suitable means for accomplishing this is by sonication.

Cells from a known volume of culture broth are resuspended in 0.05 molar phosphate buffer (pH 7.5). The suspension is then sonified using a Branson Sonifier Model 185-1) (20 k.c.) until the microbial cells of the same are sufficiently disrupted so that the isomerase enzyme is substantially all liberated. Holding the sample tube in an ice bath during sonication prevents overheating and enzyme inactivation. The resulting enzyme preparation is a solution of solubilized isomerase.

The assay procedure involves making a spectrophotometric determination of the ketose produced from a dextrose solution under a standardized set of conditions. A stock solution is made up in the following manner.

TABLE 1

STOCK SOLUTION FOR ASSAY

| Component: | | Amount |
|---|---|---|
| 0.1 M MgSO$_4$·7H$_2$O | ml | 1 |
| 0.01 M CoCl$_2$·6H$_2$O | ml | 1 |
| 1 M phosphate buffer, pH 7.5 | ml | 0.5 |
| Anhydrous D-glucose | g | 1.44 |
| Distilled water to make up a total volume of 7.5. ml. | | |

The enzyme preparation to be assayed is first diluted to contain from 1 to 6 isomerase units per ml.

An enzymatic isomerization is conducted by adding 1 ml. of the enzyme preparation to 3 ml. of the stock solution, and incubating for 30 minutes at 60°C. At the end of the incubation period, a 1 ml. aliquot is taken and quenched in a 9 ml. volume of 0.5 N perchloric acid. The quenched aliquot is then diluted to a total volume of 250 ml. As a control, for comparative purposes, a D-glucose blank is also run by substituting 1 ml. of water for the 1 ml. of the enzyme preparation in solution form, at the beginning of the incubation period.

The ketose is then determined by a cysteine-sulfuric acid method. For the purpose of this assay, one isomerase unit is defined as the amount of enzyme activity that is required to produce one micromole of levulose per minute under the isomerization conditions described.

THE RESIN CARRIERS

The macroreticular or porous-type strongly basic anion exchange resins used in the invention are described below.

By porous-type ion exchange resins are meant those ion exchange resins having many pores. Such ion exchange resins are generally adapted for adsorption. Macroreticular type ion exchange resins are commonly designated as the MR type, and have relatively large pores. By strongly basic anion exchange resins, we refer to resins having —N—(CH$_3$)$_3$X as the ion exchange group and these are distinguished from those having

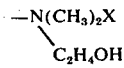

as the ion exchange group.

Amberlite IRA-904 and IRA-938 (Rohm & Haas Co., U.S.A.) are commercially available as MR type strongly basic anion exchange resins, and Diaion PA-308 and PA-304 (Mitsubishi Chemical Co., Japan) as porous-type strongly basic ion exchange resins.

The resin or polymer particles are most desirably used in the form of granules or beads and are further, usually, in the range of 16 to 100 mesh particle size (U.S. Standard Screen Series) and more preferably in the form of 20 to 50 mesh beads. For convenience of use the beads are placed or arranged in a column.

Macroreticular resins are characterized by the presence, throughout the polymeric matrix, of a network of "extra-gellular" microchannels or pores. While these micro channels are very small, they are large in comparison with the pores in conventional homogeneous cross-linked gells. Macroreticular resins suitable for use in the present invention may have specific surface areas of up to 2,000 sq. meters per gram or more.

The surface area and porosity (often reported as ml./ml. or cc./cc.) as well as other physical characteristics of macroreticular resins can be measured according to accepted procedures, for example, see pages 152–167 of "Oxidation-Reduction Polymers," Harold G. Cassidy et al., Interscience Pub. N.Y., N.Y., 1965.

In order to produce the high porosity and high specific surface areas required of the resins in the present invention, the suspension polymerization procedures of British Pat. No. 932,126 may be employed, and the disclosure of the specification of that application is incorporated herein by reference.

PREPARATION OF IMMOBILIZED ISOMERASE

Next, the method of having dextrose isomerase adsorbed on these anion exchange resins is explained. The isomerase is use in the form of solutions: 0.01 – 0.1 M tris-HCl or phosphate buffer solutions; salt solution such as $(NH_4)_2SO_4$, $MgCl_2$ or $KNO_3$ solution, all adjusted to pH 6 – 9 (preferably pH 7 – 8); or simply in water or in dextrose solutions; all having concentrations ranging from 3 to 50 units/ml.

The ion exchange resin is packed in a column of the proper size and then equilibrated by passing the same solution as used for dissolving the isomerase through the column at a flow rate between 1 SV and 3 SV for 5 – 10 hours (the term "SV" is an abbreviation for substrate velocity, and refers to the flow rate in bed volumes per hour; one bed volume is the volume of substrate per hour that is equivalent to the column volume that is taken up by the resin in the column). Then, an amount of the dextrose isomerase solution corresponding to 10 – 100 units (preferably 50 units) of the enzyme per g. of wet resin is passed through the resin column at a flow rate between 1 SV and 3 SV. After all of the enzyme solution has passed through the column, water is passed through the column to wash away unadsorbed isomerase.

Next, the resin is taken out of the column and measured for its isomerase activity.

An evaluation is described below in order to demonstrate that MR type or porous type strongly basic anion exchange resins excel in the ability of adsorbing and immobilizing dextrose isomerase.

ISOMERASE ADSORPTION

Three gram portions of each of several commercial ion exchange resins (Amberlite, Diaion) (moist) were packed in several different columns respectively. After the resins had been equilibrated thoroughly with a 0.05 M tris-HCl buffer solution (pH 7.5) a solution of 250 units of crystalline dextrose isomerase in the same buffer solution was passed through each of the columns at a flow rate of SV 3.

When all the isomerase solution has been passed through, each of the resin columns was washed with water. Then, the resins were taken out of their respective columns and measured for their enzymic activity. The results are shown in Table II.

TABLE II

| Classification | Fundamental Type | Ion Exchange Group | Name of Resin | Effective pH Range | Amount of Enzyme Adsorbed (Unit/g of wet resin) |
|---|---|---|---|---|---|
| Strongly Acid Cation Exchange Resin | Gel | $-SO_3M$ | Diaion SK-1B | 0 – 14 | 0 |
| " | Porous | " | Diaion PK-204 | " | 0 |
|  |  |  | Amberlite IR-118 |  | 0 |
|  | MR | " | Amberlite IR-124 | " | 0 |
| Weakly Acid Cation Exchange Resin | Porous | $-COOM$ | Diaion WK-10 | 5 – 14 | 0 |
|  | MR | " | Amberlite CG-50 | 4 – 14 | 0 |
| Strongly Basic Anion Exchange Resin | Gel | $-N-(CH_3)_3X$ | Diaion SA-11A | 0 – 14 | 0.4 |
|  |  | " | Amberlite IRA-400 | " | 0 |
|  | Porous | " | Diaion PA-304 | " | 10 |
|  |  | " | Diaion PA-308 | " | 19 |
|  | MR | " | Amberlite IRA-900 | " | 6 |
|  |  |  | IRA-904 |  | 24 |
|  |  |  | IRA-938 | " | 21 |
| Strongly Basic Anion Exchange Resin | Gel | $-N-(CH_3)_2X$ $\diagdown C_2H_4OH$ | Diaion SA-21A | " | 0.4 |
|  |  |  | Amberlite IRA-410 | " | 0.1 |
|  | Porous | " | Diaion PA-404 | " | 2 |
|  |  |  | Amberlite IRA-411 | " | 2 |
|  | MR | " | Amberlite IRA-911 | " | 2 |
| Intermediately Basic Anion Exchange Resin | Gel | $-N(R)_2$ | Amberlite IRA-68 | 0 – 9 | 0.2 |
| Weakly Basic Anion Exchange Resin | Gel | $-NH(R)$ | Diaion WA-11 | " | 0.8 |
|  |  | $-N(R)_3-NH(R)_1-NH_2$ | Amberlite IR-45 | " | 1 |
|  | Porous | $-N(R)_2$ | Diaion WA-30 | " | 9 |
|  | MR | $-N(R)_2$ | Amberlite IRA-93 |  | 17 |

As is clear from Table II, cation ion exchange resins had no adsorbing ability. However, MR type or porous type strongly basic and weakly basic anion exchange resins excelled in their ability to adsorb dextrose isomerase. As is explained below, however, the weakly basic anion exchange resins appear to be unsuitable for use in the present invention.

ISOMERIZATION

Explained below is a method of isomerizing dextrose with immobilized isomerase, in accordance with this invention.

Examples of dextrose to be used as materials are: crystalline dextrose (dextrose content: above 99%); powdered dextrose (dextrose content: around 90%); glucose syrup (40% – 90% dextrose); and hydrol (50% – 60% dextrose).

These kinds of dextrose are each dissolved at a concentration between 30% and 70% (preferably around 60%) and mixed with 0.001 – 0.01 M $MgCl_2$. Then, the resulting sugar solution is adjusted to a pH value of about 8.0 with NaOH or KOH. Here MgCl$_2$ plays the role of an activator of the isomerase. Meanwhile, immobilized isomerase, prepared on an MR type or porous type strongly basic anion exchange resin, as described above, is packed in a column. With the column kept at temperatures between 60°C and 70°C, the dextrose-containing solution is passed through it.

The levulose concentration of the effluent is determined by measuring the optical rotation of the solution with a polarimeter or by the cysteine —H$_2$SO$_4$—carbazole method. In the case of isomerizing dextrose with immobilized isomerase obtained in accordance with this invention, it is very important to adjust the dextrose solution to a pH value around 8.0 because the stability of the immobilized enzyme is increased as the result.

To demonstrate, ten grams of Amberlite IRA-904, which is an MR type strongly basic anion exchange resin, was packed in each of several different columns. Each column was equilibrated with a 0.05 M tris-HCl buffer solution (pH 7.5) containing 0.01 M MgCl$_2$. After the equilibration, a solution of 1,000 units of crystalline isomerase, in the same buffer solution, was passed through each column. Then, separate 60% dextrose solutions each containing 0.01 M MgCl$_2$ adjusted to different pH values of 6.0, 7.0, 8.0, and 9.0 respectively, were passed through the columns at 60°C – 70°C and at a flow rate of about SV 1.

After this isomerizing process, the levulose content of the effluent from each of the columns was measured. The results obtained are shown in FIG. 1, where the vertical scale is the levulose content and the horizontal axis is the operating time for each column, in days.

In FIG. 1, the letter *a* identifies the line that is the plot for the levulose content of the effluent of the column operated at pH 8.0; the letter *b* identifies the pH 7.0 column; the letter *c*, the pH 6.0 column; and the letter *d*, the pH 9.0 column. As is clear from the figure, it is desirable to hold the pH value of the dextrose solution to be isomerized around 7.0 – 8.5 in order to keep the immobilized isomerase stable during the isomerizing reaction, and the immobilized isomerase is most stable at about pH 8.

If the continuous isomerizing reaction is carried out at about pH 8.0, the equilibrium rate of isomerization (52% levulose) is maintained for 15 days. After that, however, the rate lowers gradually, dropping to one-half of the initial value (26%) in 22 days. The time in which the rate of isomerization of an immobilized isomerase drops to one-half of the initial value is defined as its "half-life".

As will be demonstrated hereafter, the purity of the dextrose isomerase, that is used for immobilization, has little effect on the stability of the resulting immobilized isomerase, during the isomerizing reaction.

Several columns were packed with 12g each of Amberlite IRA-904 (wet), which is an MR type strongly basic anion exchange resin. After the resin had been equilibrated thoroughly with a 0.01M MgCl$_2$ solution (pH 7.5), the columns were supplied, respectively, with: a solution of 1,000 units of crude isomerase (extracted from cells by autolysis); partially purified glucose isomerase (separated from nucleic acid by protamine treatment); and crystalline isomerase; in the same solution. Then, a glucose solution containing 0.01M MgCl$_2$(pH 8.0) was passed the column at a temperature of 70°C and at a flow rate of SV 1. The immobilized enzymes prepared from these kinds of dextrose isomerase were found to have half-lives of around 17 days each, showing no effect ascribable to the purity of the initial isomerase. In the case of preparing immobilized isomerase industrially, therefore, it is advantageous to use crude glucose isomerase.

When glucose is isomerized continuously by the methods described above, the sugar solution coming out of resin columns contains levulose accounting initially for 52% of the solid substance, as was shown in FIG. 1. This levulose content was maintained for 10 to 15 days. Now, this rate of isomerization (52%) is the equilibrium value attained when the isomerization is conducted under the conditions stated above. After that, however, the rate lowers gradually dropping to one-half of the initial value or 26% in 17 to 22 days.

COLUMN REACTIVATION FOR CONTINUOUS ISOMERIZATION

Next, the method of reactivating columns, whose isomerizing activity has begun to drop, is explained.

First, a dextrose isomerase is dissolved in the same glucose solution as that which is used for isomerization. Then, an amount of the resulting enzyme solution, containing 10 – 50 units (preferably 25 to 50 units) of isomerase per gram of wet resin, is passed through the columns at the same flow rate as that at which the glucose solution to be isomerized is passed. As it passes through the column, more enzyme is adsorbed, at the same time that the glucose is being isomerized.

In this manner, the resin columns regain their original rate of isomerization (52%). Moreover, the immobilized isomerase, which has been reactivated, shows the same "half-life" as the original one (17 – 22 days). If this procedure is repeated, it is possible to carry out the isomerization without repacking columns as long as the ion exchange resins last. Further, the levulose content in the effluent from resin columns can be held constant at a given isomerization rate up to about 52% (the normal equilibrium value) in the following way. When the isomerization rate is found to drop, as can be detected by measurement with a polarimeter, the resin column is immediately re-activated in the above manner, or, alternatively, the flow rate is gradually reduced to keep the isomerization rate constant, and then the column is re-activated at a proper time.

A favorable feature of this method of continuous isomerization is that the resulting isomerized syrup is almost colorless. Only desalting with ion exchange resins is needed for refining. No decolorizing with active carbon, before sale, is necessary.

As will now be demonstrated, the immobilized dextrose isomerase, prepared by having isomerase adsorbed on an MR type or porous type strongly basic anion exchange resins, is superior to those prepared with other ion exchange resins, for capability of reactivation.

As was described above, Amberlite IRA-904, which is an MR type strongly basic anion exchange resin, Amberlite IRA-93, which is an MR type weakly basic anion exchange resin, and Diaion WA-30, which is a porous type weakly basic anion exchange resin, excelled in the ability of adsorbing isomerase.

Ten grams of each of these resins (wet) was packed in three different columns respectively. After the resins had been equilibrated thoroughly with a 0.01M MgCl$_2$ solution (pH 7.5), a solution of partially purified isomerase (1,000 units) in the same solution was passed through each of the columns. Then, glucose containing 0.01 MgCl$_2$ (pH 8.0) was passed at 70°C through each column, at a flow rate of SV 1.

The rates of isomerization of the respective isomerase preparations made with the different ion exchange resins (percentages of levulose of the solid substance in the effluents which had come out of the different columns) were measured with a polarimeter.

All of the enzyme preparations showed a levulose value of 52% in the effluent at first. With the lapse of time, however, the value dropped gradually. When it dropped down to 26% (one-half of the initial value), a solution of 250 units of isomerase in a glucose solution containing 0.01M MgCl$_2$ (pH 8.0) was passed through the column. The isomerizing reaction was then continued by continuing to pass the original glucose solution through the column.

Figure 2:
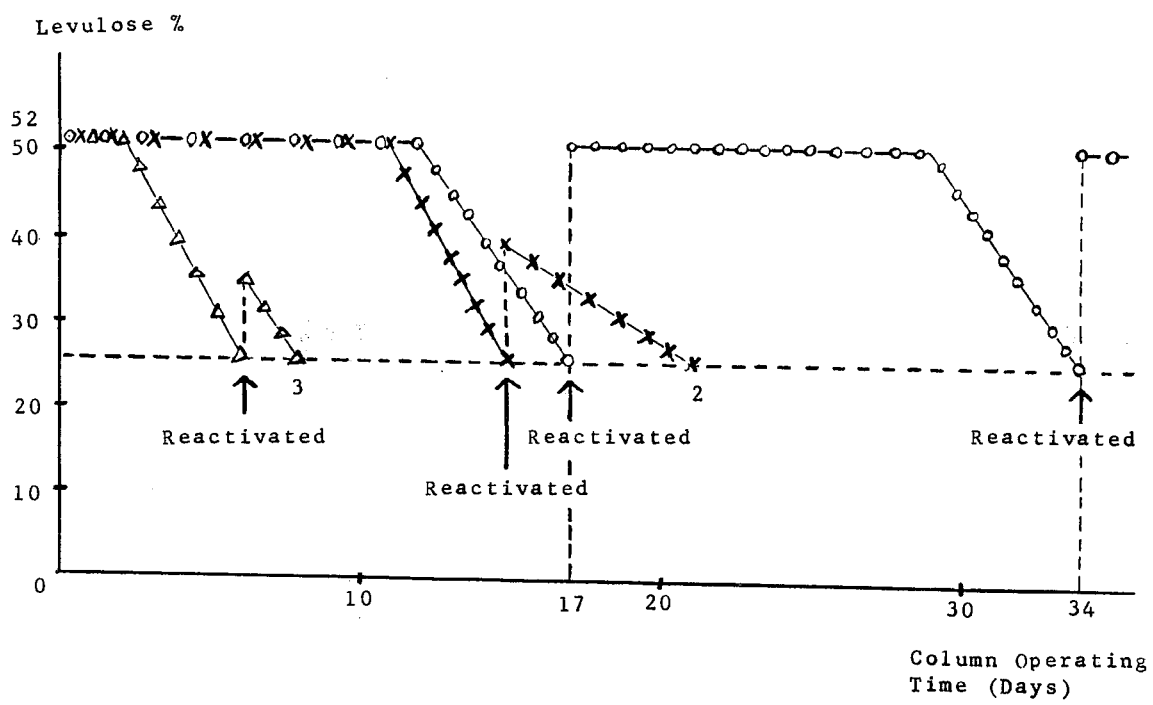

The results obtained are shown in FIG. 2. In this figure (1) shows the results for Amberlite IRA-904, (2) for Amberlite IRA-93, and (3) for Diaion WA-30.

Dextrose isomerase immobilized with Amberlite IRA-904 regained the initial rate of isomerization (52%) after reactivation. Further, after activation it showed the same half-life as initially.

In the case of immobilized isomerase prepared with Amberlite IRA-93 and Diaion WA-30, on the other hand, a complete regeneration of the initial rate of isomerization was not achieved. The activity after reactivation increased only a little as is shown in FIG. 2, when these weakly basic anion exchange resins were used as the carriers.

The invention will now be demonstrated by several specific examples. All parts and percentages herein are by weight, unless otherwise specified.

EXAMPLE 1

CONTINUOUS ISOMERIZATION WITH THE ENZYME IMMOBILIZED ON AMBERLITE IRA-904

Fifty grams of moist Amberlite IRA-904, which is an MR type strongly basic anion exchange resin, was packed in a column (2.5 × 20 cm). With the resin equilibrated with a 0.01M MgCl$_2$ solution adjusted to pH 8.0, 3,000ml of a solution of crude dextrose isomerase in the same solution (containing 5,000 units of isomerase) was passed through the column at a flow rate of SV 3. After all the isomerase solution had been passed through the column, a 60% dextrose solution containing 0.01M MgCl$_2$ and adjusted to pH 8.0 was passed through the column at a flow rate of SV 1 at 70°C.

The rate of isomerization was measured with a polarimeter and expressed as the percentage of levulose of the solid substance in the effluent from the column. The rate remained 52% (equilibrium value) for the first 12 days. After that, however, it lowered gradually and dropped to 26% on the 17th day.

At this time, 1,500ml of a solution of isomerase in a 60% dextrose solution containing 0.01M MgCl$_2$ and adjusted to pH 8.0 (corresponding to 2,500 units of isomerase) was passed through the column at a flow rate of SV 1. Then, the isomerizing reaction was continued on by passing the same dextrose solution (without isomerase) through the column under the same conditions as those used for the isomerizing reaction.

As the result of this procedure, the resin column regained its original rate of isomerization of 52%, and retained this value for further 12 days. In the succeeding 5 days, however, the rate of isomerization dropped to 26%. At this time, the resin column was again reactivated in the same manner. It was again returned completely to its initial activity.

EXAMPLE 2

CONTINUOUS ISOMERIZATION WITH ENZYME IMMOBILIZED ON DIAION PA-308

Fifty grams of moist Diaion Pa-308, which is a porous type strongly basic anion exchange resin, was packed in a column (2.5 × 2.0cm). After the resin had been equilibrated with a 0.01M MgCl$_2$ solution adjusted to pH 8.0, 200 ml of a solution of partially purified dextrose isomerase in the same solution (containing 5,000 units of isomerase) was passed through the column at a flow rate of SV 1.

Then, a 60% dextrose solution containing 0.01M MgCl$_2$ and adjusted to pH 8.0 was passed through the column at a flow rate of SV 3 with the column kept at 70°C. The rate of isomerization was measured continuously with a polarimeter. It remained at 52% for the initial 3 days, and began to drop gradually thereafter. At that time, the flow rate of the dextrose solution was lowered so that the rate of isomerization could be held at 52%. This procedure was made possible by reducing the flow rate of the dextrose solution by SV 0.25 every day.

Ten days after the time when the reduction of the flow rate was started (when the flow rate dropped down to SV 0.5), 100ml of a solution of isomerase in a 60% dextrose solution containing 0.01M MgCl$_2$ and adjusted to pH 8.0 (corresponding to 2,500 units of glucose isomerase) was passed through the column at a flow rate of SV 0.5. After that, the isomerizing reaction was continued or by passing the dextrose solution (without isomerase) through the column at the initial flow rate, namely, at SV 3. By repeating this procedure, it was possible to continue the isomerization at a rate of isomerization of 52% as long as the ion exchange resin lasted. It was unnecessary to repack the column during the period.

EXAMPLE 3

CONTINUOUS ISOMERIZATION WITH ENZYME IMMOBILIZED ON AMBERLITE IRA-904

Fifty grams of moist Amberlite IRA-904 resin, which is an MR type strongly basic anion exchange resin, was packed in a 2.5 × 20 cm column (Bed volume: 75 ml). The resin was equilibrated with 0.01 M MgCl$_2$ solution, pH 8.0, and then 200 ml of isomerase solution, containing 5,000 units of isomerase, was passed through the column at a flow rate of SV 1.

After all the isomerase solution had been passed through the column, 60% dextrose solution, pH 8.0, containing 0.01 M MgCl$_2$ was passed through the column at a flow rate of SV 2.5, at 60°C. The isomerization rate of the effluent was continuously measured with a polarimeter. The isomerization rate was found to be 45% at first and it was held constant (45%) by reducing the flow rate of the dextrose solution by SV 0.04 per day. When the flow rate dropped down to SV 0.5 after 50 days, 5,000 units of isomerase, dissolved in 200 ml of the dextrose solution, was passed through the column at SV 0.5 to re-activate the resin.

Then, the isomerization reaction was continued by passing the dextrose solution (without isomerase) through the column at a flow rate of SV 2.3, which gave a 45% isomerization rate. The flow rate was reduced in the same way as above-mentioned. By repeating this procedure, it was possible to continue the isomerization at the 45% level, as long as the resin lasted.

CONCLUSION

Immobilized enzyme preparations, in accordance with the present invention, generally can be used to isomerize dextrose at a pH in the range from about 6 to about 9, and at a temperature in the range from about 20°C to about 80°C. However, and while the processes of this invention are not necessarily confined to these ranges, more preferred ranges for pH are 7.0 to 8.5, or most preferably, 8.0, and for temperature, 60°C to 70°C. The dextrose solution, to be isomerized, can be almost any desired workable concentration. For practical purposes, generally 40% sugar concentration, in a glucose syrup, represents the upper limit of practical workability. However, the process is operative at any concentration at which contact occurs, whether in a batch or continuous configuration.

The resins that are used, in the practice of this invention, are particulate in form, to permit good hydraulic properties in the isomerization reactor. The resin particles are characterized by the presence, throughout the polymeric matrix of each particle, of a network of pores that provide a high surface area for adsorption and contact.

While the immobilized enzyme composits have been described herein as used in a column, they are useful for isomerization in any form in which they are conveniently brought into contact with the dextrose supply liquor. Thus, columns, filter presses, or any kind of contact devices or systems may be employed.

While the invention has been described in connection with specific embodiments thereof, it will be understood that it is capable of further modification, and this application is intended to cover any variations, used, or adaptions of the invention following, in general, the principles of the invention and including such departures from the present disclosure as come within known or customary practice in the art to which the invention pertains and as may be applied to the essential features hereinbefore set forth, and as fall within the scope of the appended claims.

What is claimed is:

1. A process for the continuous isomerization of dextrose to levulose comprising:
    passing a solution containing dextrose, at a pH of from about 7.0 to about 8.5, through a bed of immobilized dextrose isomerase prepared by bringing a solution of dextrose isomerase into contact with a porous or macroreticulated strongly basic anion exchange resin having -N-$(CH_3)_3$-X as the ion exchange group;
    removing a levulose-bearing solution from the bed until a decrease in enzyme activity occurs, then passing additional dextrose isomerase through the bed to reactivate said bed,
    continuing to pass the solution containing dextrose through the reactivated bed, and
    recovering additional levulose-bearing solution therefrom.

2. A process in accordance wth claim 1 wherein the fresh dextrose isomerase is brought into contact with the particulate resin while mixed in the solution containing dextrose that is being brought into contact with the composite.

3. A continuous process for preparing a levulose-bearing product comprising:
    continuously passing a solution containing dextrose at a pH in the range from about 7.0 to about 8.5 through a bed of an immobilized dextrose isomerase composite wherein the dextrose isomerase is immobilized on a particulate strongly basic anion exchange resin having —N—$(CH_3)_3$—X as the ion exchange group that is characterized by the presence throughout its polymeric matrix of a network of pores that provide an adsorptive surface area;
    continuously removing from the bed a levulose-bearing product until a decrease in activity of the original composite occurs;
    adding fresh dextrose isomerase to the feed stream of the solution containing dextrose and passing the mixture thereby obtained through said bed into contact with the composite to enhance the activity of the composite without interrupting isomerization, and
    continuously thereafter recovering additional levulose-bearing product from the bed.

4. A process in accordance with claim 3 wherein the pH is about 8.0.

5. A process in accordance with claim 3 wherein the particulate resin is a macroreticular, strongly basic anion exchange resin.

6. A continuous process for the enzymatic production of a levulose-bearing product, comprising:
    continuously passing a dextrose-containing solution at a pH from about 6 to about 9, at a temperature in the range from about 20°C. to about 80°C. and having a dextrose concentration in the range of between 30% and 70%, d.s., at a flow rate of from 1 to about 5 SV, wherein "SV" is the substrate velocity of the dextrose-containing solution measured in bed volumes per hour, through a bed containing an immobilized dextrose isomerase composite, wherein the immobilized dextrose isomerase composite comprises dextrose isomerase immobilized onto a macroreticular synthetic strongly basic anion exchange resin having -N-$(CH_3)_3$-X as the ion exchange group in the form of granules or beads having a particle size in the range from about 16 mesh to about 100 mesh (U.S. Standard Screen) and characterized by the presence, throughout the polymeric matrix of its particles, of a network of pores that provide an adsorptive surface area up to about 2,000 square meters per gram, continuously removing a substantially colorless, levulose-bearing product from the bed, and
    maintaining the isomerase activity of said immobilized dextrose isomerase by adding a solution containing from 10 to about 50 units per gram of isomerase activity per wet gram of resin to said dextrose-containing solution.

\* \* \* \* \*